United States Patent [19]
Pavlak

[11] Patent Number: 5,718,002
[45] Date of Patent: Feb. 17, 1998

[54] HEARING PROTECTIVE EYEWEAR

[76] Inventor: Ronald M. Pavlak, 1063 Kirkwood Dr., Eagan, Minn. 55123

[21] Appl. No.: 779,682

[22] Filed: Jan. 7, 1997

[51] Int. Cl.$^6$ ............................. A61F 9/00; G02C 5/14
[52] U.S. Cl. .................... 2/423; 2/13; 2/449; 351/123
[58] Field of Search ...................... 2/423, 448, 449, 2/450, 451, 12, 13, 15, 209, 184.5, 174, 9; 351/123, 158, 47, 111

[56] References Cited

U.S. PATENT DOCUMENTS

| | | | |
|---|---|---|---|
| 1,117,968 | 11/1914 | De Bobory | 2/426 |
| 1,468,556 | 9/1923 | Camp et al. | 2/423 |
| 1,621,629 | 3/1927 | Dawson | 2/448 |
| 2,140,630 | 12/1938 | Illguth | 2/6 |
| 2,593,892 | 4/1952 | Kindel | 2/174 |
| 3,173,147 | 3/1965 | Gross et al. | 2/14 |
| 3,226,729 | 1/1966 | Fucci | 2/12 |
| 3,932,031 | 1/1976 | Johnston | 351/47 |
| 3,943,925 | 3/1976 | Leight | 128/152 |
| 4,670,911 | 6/1987 | Dunford | 2/209 |
| 4,751,746 | 6/1988 | Rustin | 2/13 |
| 5,044,014 | 9/1991 | Cornale et al. | 2/423 |
| 5,086,789 | 2/1992 | Tichy | 128/866 |
| 5,133,596 | 7/1992 | Korny et al. | 351/158 |
| 5,201,856 | 4/1993 | Edwards | 2/209 |
| 5,278,999 | 1/1994 | Brown et al. | 2/209 |
| 5,323,493 | 6/1994 | Ogiba | 2/422 |
| 5,388,269 | 2/1995 | Griffin | 351/123 |
| 5,394,567 | 3/1995 | Vatterott | 2/13 |
| 5,438,706 | 8/1995 | Lambur | 2/449 |
| 5,477,564 | 12/1995 | Tichy | 2/423 |
| 5,619,750 | 4/1997 | Allewalt | 2/449 |

FOREIGN PATENT DOCUMENTS

| | | | |
|---|---|---|---|
| 753789 | 3/1967 | Canada | 2/449 |
| 611274 | 10/1960 | Italy | 2/451 |

*Primary Examiner*—Amy B. Vanatta
*Attorney, Agent, or Firm*—Michael S. Sherrill

[57] ABSTRACT

Eye and ear protective eyewear comprising a standard pair of conventional reading glasses, prescription glasses, safety glasses or sunglasses to which a pair of wind-deflecting deflectors are attached to the lenses and/or frame and extend rearward from the lenses towards the ear. The deflectors are configured and arranged to deflect air flow away from the ear while terminating prior to the auditory meatus of the ear in order to avoid interfering with the hearing of the wearer.

24 Claims, 4 Drawing Sheets

HEARING PROTECTIVE EYEWEAR

FIELD OF THE INVENTION

The invention relates eyewear. More specifically, the invention relates to eyewear for the sports enthusiast.

BACKGROUND

Protective eyewear has been used for years in various sports, including high speed sports such as motocross, skiing and skydiving; contact sports such as basketball, hockey and football; and sports involving a fast-moving projectile such as racquet ball, splat-ball and squash. More recently, similar eyewear has been used in other sports such as bicycling and running, as well as various leisure activities such as sailing and hiking. Such eyewear primarily focuses upon preventing any damage caused by a blow to the eye, and secondarily focuses upon preventing eye strain such as caused by glare or the constant movement of air. However, none of these protective sports glasses protect the ears against the deleterious effects of air being constantly blown into the ear, which is often annoying and occasionally painful.

Various efforts have been made to develop ear protective devices, including various designs which incorporate eye and ear protection into a single device. Examples of such designs are described in U.S. Pat. Nos. 1,117,968, 1,621,629, 2,593,892, 3,173,147, 3,943,925, 4,751,746, 5,133,596, 5,201,856, 5,278,999, and 5,323,493. Unfortunately, such designs are cumbersome, expensive, unappealing and/or significantly interfere with the ability to hear. Of particular interest is the cumbersome and unsightly eyewear described in U.S. Pat. No. 5,323,493, which includes U-shaped air deflector structures attached to the ends of a head band and a mechanism for allowing the headband to be attached to a pair of eyeglasses. The headband is essential to operation of the apparatus as it holds the deflector structures tight against a wearers temples in order to prevent air from flowing between the deflectors and the temples.

Accordingly, a substantial need exists for inexpensive and attractive eyewear which is capable of protecting both the eyes and the ears during various sporting activities without reducing vision or impairing hearing.

SUMMARY OF THE INVENTION

I have discovered unique eyewear which is both fashionable and functional. The eyewear protects both the eyes and ears from the wind and various oncoming foreign bodies, such as rain, sand and insects. The eyewear is also compatible with standard bicycle helmets.

The eyewear is based upon a standard pair of conventional reading glasses, prescription glasses, protective eyewear or sunglasses (i.e., a pair of transparent lenses, a nosepiece and a pair of rearwardly extending bows attached directly or indirectly to the lenses). The eyewear further includes a pair of wind-deflecting deflector s attached directly or indirectly to the lenses (e.g., the deflector s may be attached to a frame which is attached to the lenses) and extending rearward from the lenses in substantially parallel relationship to the bows. The deflector s are configured and arranged to guide rearwardly-directed air flow away from the ear and terminate prior to the auditory meatus of the ear. The eyewear is thereby able to protect both the eyes and the ears of a wearer without substantially interfering with the hearing of the wearer.

DETAILED DESCRIPTION OF THE INVENTION INCLUDING A BEST MODE

Nomenclature

10 Eyeglasses
20 Lenses
20r Right Lens
20s Left Lens
21 Inside Edge of Lenses
21r Inside Edge of Right Lens
21s Inside Edge of Left Lens
22 Outside Edge of Lenses
22r Right Outside Edge of Lens
22s Left Outside Edge of Lenses
23 Top of Lenses
25 Bridge
30 Nosepiece
40 Bows
40r Right Side Bow
40s Left Side Bow
45 Hinge Connecting Bow to Lens
45r Right Side Bow Hinge
45s Left Side Bow Hinge
60 Deflectors
60r Right Side Deflector
60s Left Side Deflector
61 Front Edge of Deflector
62 Rear Edge of Deflector
63 Top Edge of Deflector
64 Bottom Edge of Deflector
65 Hinge Connecting Deflector to Lens
65r Right Side Deflector Hinge
65s Left Side Deflector Hinge
67i Inside Wall of Deflectors
67o Outside Wall of Deflectors
68 Channel Formed between Inside and Outside Wall
68f Front End of Channel
68r Rear End of Channel
69 Air Intake Vent for Channel
70 Snap
80 Side Pads
81 Vertical Side Pad
90 Front Pad
100 Wearer
101 Wearer's Face
200 Ears

Construction

Figure 1:
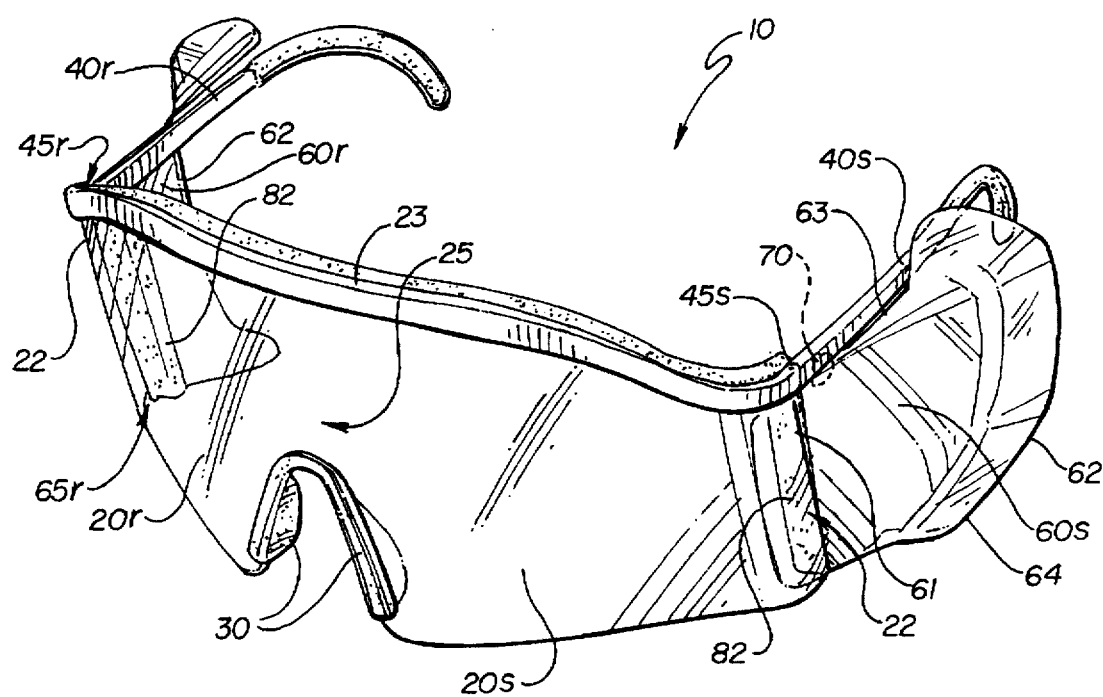
FIG. 1 is a perspective view of one embodiment of the invention.
Figure 2:
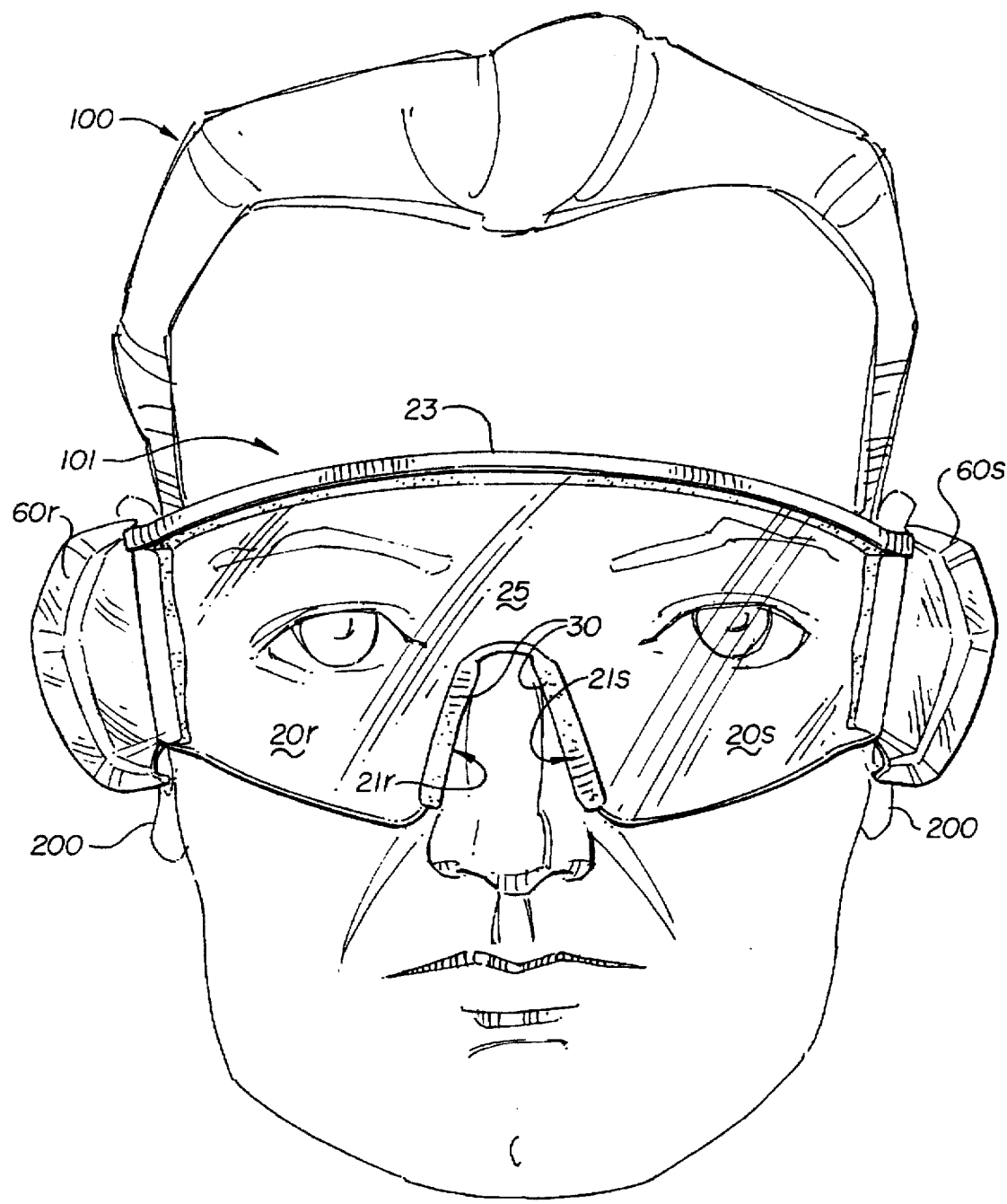
FIG. 2 is a front view of the invention as shown in FIG. 1.
Figure 3:
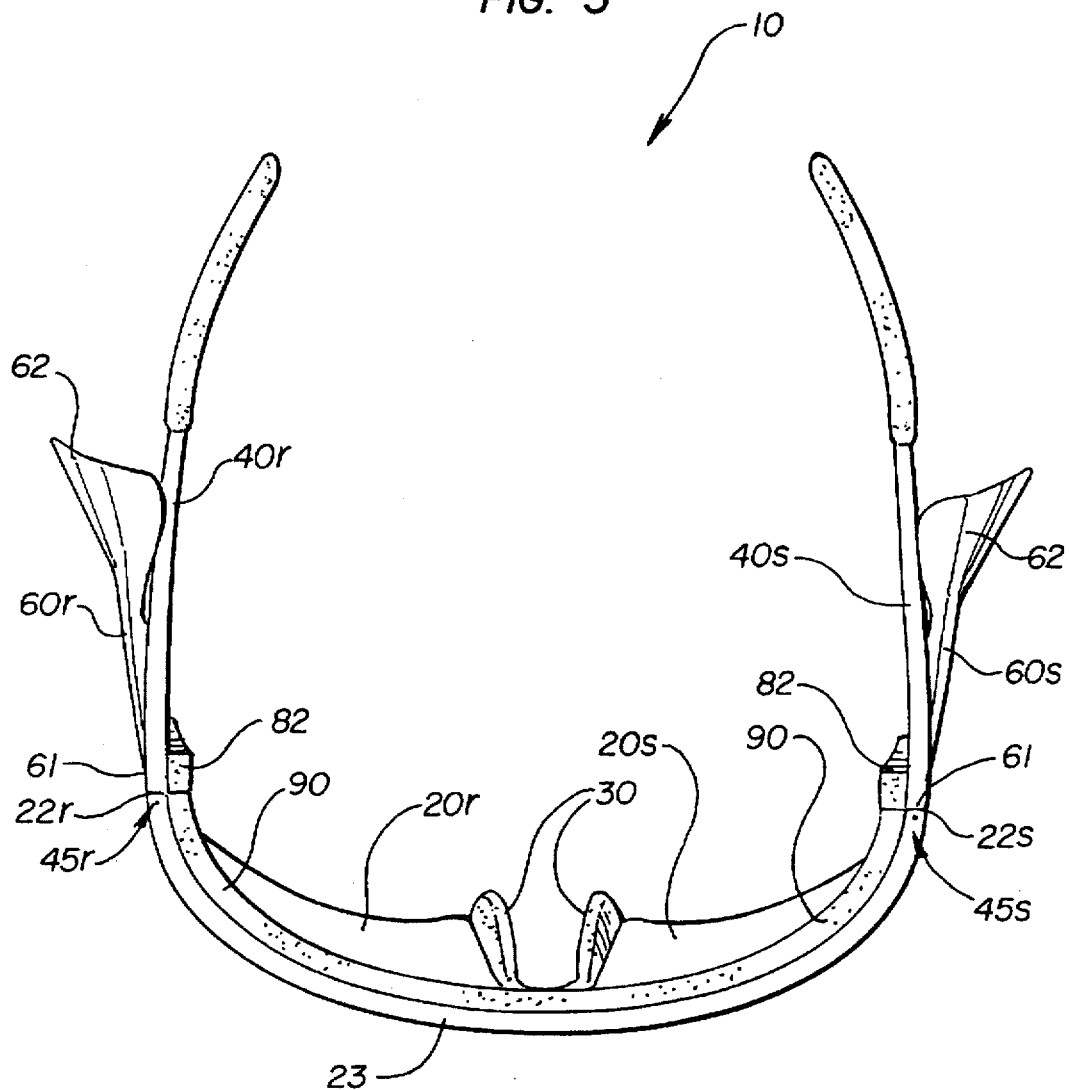
FIG. 3 is a top view of the invention as shown in FIG. 1.

Referring to FIGS. 1 through 3, the protective eyeglasses 10 include a standard pair of lenses 20, a nosepiece 30, and a pair of bows 40. The eyeglasses 10 may be selected from any of the various conventional glasses, including reading glasses, prescription glasses and sunglasses. The eyeglasses 10 shown in FIGS. 1 through 5 are a pair of sunglasses. Without intending to be unduly limiting, further discussion of the invention will be based upon the embodiment of the invention as shown in FIGS. 1 through 5 (e.g., sunglasses having lenses formed from a single sheet of material).

Eyeglasses

Lenses

The lenses 20 can be formed from any of the conventional materials used in the construction of reading glasses, prescription glasses, protective eyewear or sunglasses. Such materials includes specifically, but not exclusively, transparent polymeric materials such as polycarbonates and polyolefins, and glass.

The lenses 20 can be configured into substantially any desired shape from separate right 20r and left 20s oval lenses (not shown), to right 20r and left 20s lenses 20 formed from a single sheet of material as shown in FIGS. 1 through 5, wherein the lenses 20 are shaped to create the bridge 25 of the eyeglasses 10. The design options for the lenses 20 are virtually endless, dependent only upon the contours of a wearer's face 101 and the imagination of the designer.

Nosepiece

As with the lenses 20, the nosepiece 30 can be selected from any of the conventional nosepieces known in the industry, from a simple flange formed from the inside edge 21 of each lens 20, to an elaborate assembly of a supple pad (not shown) rotatably mounted within an adjustable post (not shown). The nosepiece 30 shown in FIGS. 1 through 3 and 5 is formed from an elastomeric material which includes a longitudinal channel (not shown) for accommodating insertion of an edge portion of the lenses 20. The nosepiece 30 is contoured to fit within the arch formed in the lenses 20 and is permanently attached to the lenses 20 by an adhesive.

A particularly well suited nosepiece 30 is one which is capable of conforming to the contours of a wearer's face when the glasses 10 are pressed onto the wearer's face under a modest pressure of about two to ten times the normal gravitational force exerted upon the wearer's face by the glasses 10. One such type of nosepiece 30 comprises a mass of a readily conformable yet cohesive material, such as modeling clay or a soft wax, retained within a nontacky pliable coating, such as a thin layer of a natural or synthetic foamed rubber. This same type of conformable material can be used to cover that portion of each bow 40 which contacts the ears (not shown).

Bows

As shown in FIGS. 1 and 3 through 5, standard bows 40 are attached to the outside edges 22 of the lenses 20 via hinges 45 to form a conventional pair of eyeglasses 10. The bows 40 can be attached to the lenses 20 directly or indirectly, such as through a frame (not shown).

Frames

Depending upon the desired strength and design of the eyeglasses 10, a conventional frame (not shown) may be provided to which the lenses 20, nosepiece 30 and bows 40 are attached. The frames (not shown) may be constructed from the various materials commonly used to construct eyeglass flames, including various plastics and metals.

Deflectors

As shown in FIGS. 1 through 5, a pair of wind-deflecting deflectors 60 are attached directly or indirectly to the lenses 20 and extend rearward from the lenses 20 in substantially parallel relationship to the bows 40.

Figure 4:
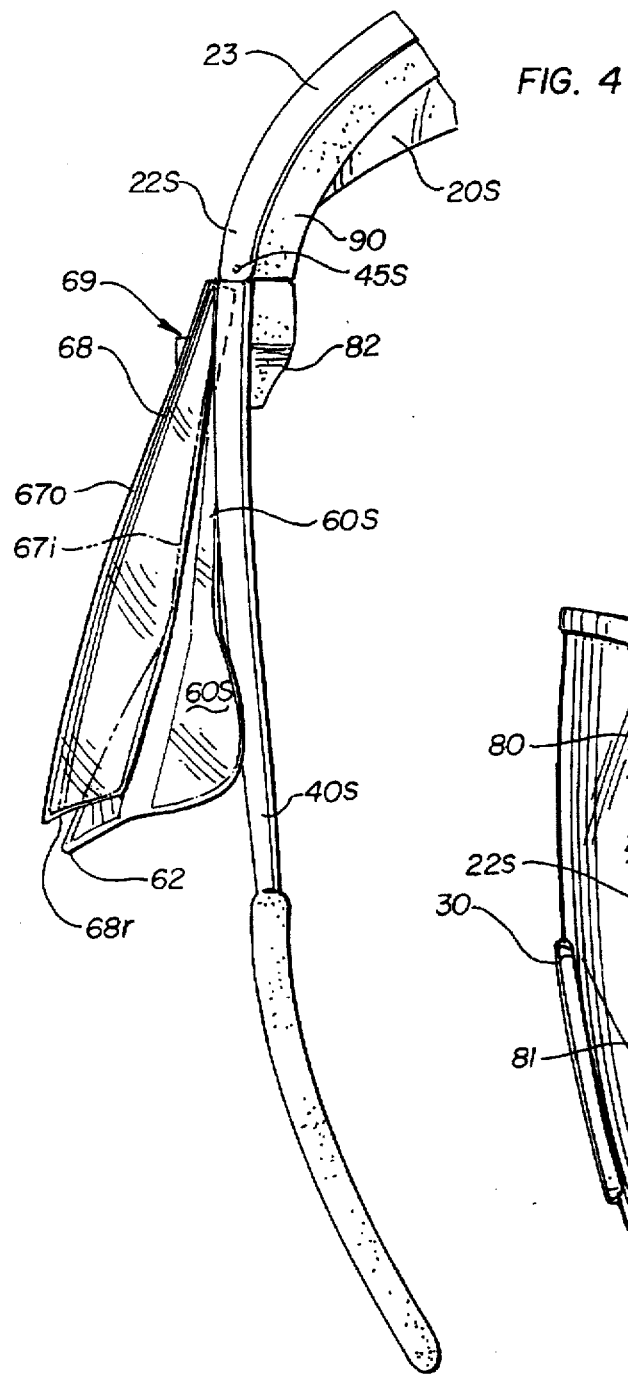
FIG. 4 is an enlarged top view of a left side portion of a second embodiment of the invention.

As shown best in FIGS. 2 through 4, the deflectors 60 are configured to direct oncoming air away from the ears 200 (e.g., curved away from the wearer's face 101) without covering the ears 200. By positioning the rear edge 62 of each deflector 60 forward of the auditory meatus (not shown) of the ear 200, the deflectors 60 are able to prevent oncoming air-flow from striking the ears 200, without substantially interfering with the hearing of the wearer 100. This feature is particularly useful when the wearer 100 is involved in an activity where the wearer's face 101 is subjected to a continuous oncoming wind of greater than about 10 miles per hour, such as bicycling, motorcycling and sailing. The outward curvature of the deflectors 60 away from the face 101 of a wearer 100 facilitates the passage of a side strap (not shown) of a standard bicycle helmet (not shown) between the deflectors 60 and the face 101 of a wearer 100.

The deflectors 60 are preferably attached to the lenses 20 or frame (not shown) by the same hinged mechanism 65 used to connect the bows 40. This permits the deflectors 60 to be folded inward along with the bows 40 for storage. The deflectors 60 are also preferably releasably connected to the lenses 20 or frame (not shown) so that the deflectors 60 may be removed from the eyeglasses 10 when the wearer 100 wishes to wear a conventional pair of eyeglasses 10.

The deflectors 60 are optionally provided with a means for connecting the deflectors 60 to the corresponding paired bow 40 in order to provide enhanced stability to the deflectors 60. As shown in FIG. 1, a snap 70 may be employed by securing the female half of the snap 70 to the outside surface (not numbered) of the bow 40 and securing the male half of the snap 70 to the appropriate corresponding position on the paired deflector 60.

Any of a number of different connecting means may be employed, including specifically, but not exclusively: permanent means such as an adhesive or a groove in the underside of the bows 40 into which the deflector 60 is friction fitted, and releasable means such as a hook and eyelet system, hook and loop tape, and snaps.

The deflectors 60 can be configured and constructed such that oncoming wind speeds of greater than about 20 miles per hour will cause the rear portion (not numbered) of the deflectors 60 to curve towards the temples (not numbered) of a wearer 100 and thereby result in a streamlined effect as well as securing the eyeglasses 10 in position on the face 101 of the wearer 100.

The deflectors 60 may optionally be formed as a unitary feature with the lenses 20, such that the lenses 20 and deflectors 60 form a single, unitary piece.

Figure 5:
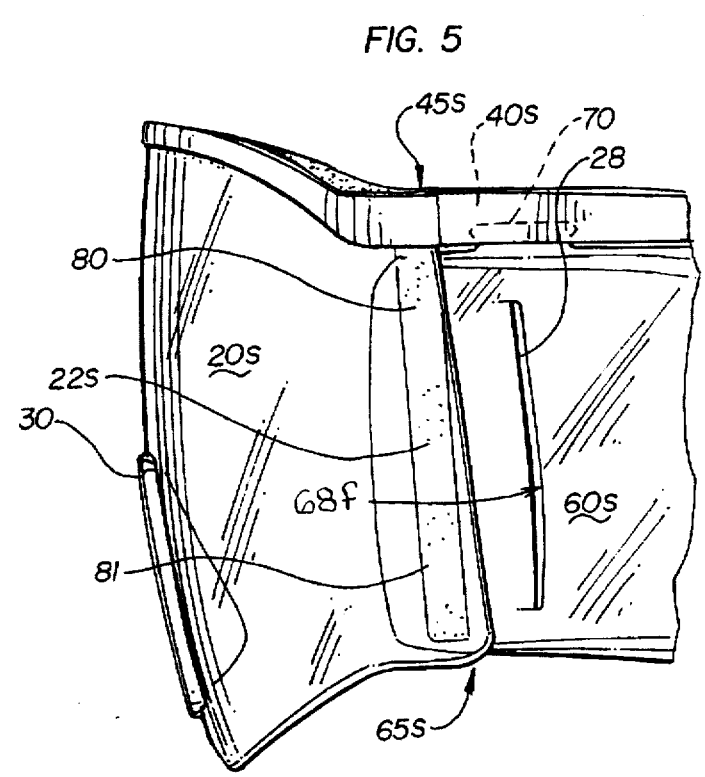
FIG. 5 is an enlarged side view of the front left side of the invention as shown in FIG. 4.

As shown in FIGS. 4 and 5, each of the wind-deflecting deflectors 60 may alternatively be configured with inner 67i and outer 67o walls which define a channel 68 therebetween extending roughly parallel to the face of a wearer. An intake vent 69 is provided at the forward edge 68f of the channel 68 to allow the flow of air into the channel 68. The rearward edge 68r of the channel 68 is open so as to allow air to flow through and exit from channel 68. Such a wind channel can provide an air curtain for the ears 200 when the wearer is traveling at a fair rate of speed (i.e., greater than 20 miles per hour) and thereby reduce the eddy effect occuring at the rearward end 62 of the deflectors 60 proximate the ears 200.

Air Vents

The eyeglasses 10 and/or the deflectors 60 may optionally be provided with air intake vents (not shown) for venting moisture from underneath the eyeglasses 10, and thereby reducing the tendency of the lenses 20 to fog, the tendency of the glasses 10 to slip on the face 101 of a wearer 100, etc. The vents should be configured and arranged to reduce the amount of foreign bodies, such as dust, passing through the vents and reaching the eyes of a wearer 100.

Side Pads

The eyeglasses 10 may optionally be provided with side pads 80 for purposes of preventing air from flowing into the spacing between the eyeglasses 10 and the face 101 of a wearer 100 and reaching the ear 200. One example of such side pads 80 are shown in FIG. 5, in which vertical side pads 81 are attached to the inner surface (not numbered) of the lenses 20 proximate the outside edges 22 of the lenses 20. Alternatively, side pads (not shown) may be attached to the inner surface (not numbered) of each deflector 60 and extend at a roughly 45° angle from the upper front edge 61,63 of the deflector 60 towards the lower rear edge 62,64 of the deflector 60. The pad would terminate a sufficient distance forward of each ear 200 so that the pad would not interfere with the straps (not shown) of a standard bicycle helmet (not shown). Such pads would provide the additional benefit of supporting the deflector 60 in position on the face 101 of a wearer 100 and dampening any vibration of the deflectors 60.

The side pads 80 may be constructed from any suitable material, such as any of the various hypoallergenic foamed plastics commonly used as a cushioning material in conventional sports eyewear.

Other Options

The eyeglasses 10 are preferably shaped to closely conform to the contours of a wearer's face 101, and may also be equipped with any of the various options commonly found on other eyewear, including specifically, but not exclusively, (i) a front foamed pad 90 along the top 23 of the lenses 20 or frame (not shown), (ii) antireflective, ultraviolet reflective and/or scratch resistant coatings on the lenses 20, (iii) tinted lenses, (iv) spring biased hinges for attaching the bows 40 to the lenses 20 or frame (not shown), (v) telescoping bows (not shown) capable of being customized to fit the face 101 of a wearer 100, etc.

I claim:

1. Auditory protective eyewear, comprising:
   (a) a pair of transparent lenses;
   (b) a nosepiece;
   (c) a rearwardly extending bow attached to each lens so as to form a pair of conventional eyewear; and
   (d) a wind-deflecting deflector attached to each lens and extending rearward from the lense in substantially parallel relationship to the corresponding bow, wherein the deflectors are configured and arranged to guide rearwardly-directed air flow away from the auditory meatus of a wearer and terminating prior to effecting coverage of the auditory meatus of a wearer, whereby the deflectors do not substantially interfere with the hearing of a wearer.

2. The eyewear of claim 1 wherein each deflector comprises inner and outer walls which define a channel therebetween having an intake vent proximate a forward end of the channel and an outlet opening proximate a rearward end of the channel, wherein the channel is effective for channeling rearwardly directed air flow through the channel and forming an air curtain over the auditory meatus of a wearer.

3. The eyewear of claim 1 wherein the eyewear further includes a pad attached to each deflector effective for contacting the face of a wearer and thereby stabilizing the eyewear when the eyewear is worn.

4. The eyewear of claim 3 wherein the pads are configured and arranged so as to block airflow occurring between a forward portion of the deflectors and a wearer's face from reaching a wearer's ear.

5. The eyewear of claim 1 wherein the eyewear further includes a frame to which the lenses, nosepiece, bows and deflectors are attached.

6. The eyewear of claim 1 wherein the eyewear is a pair of sunglasses.

7. The eyewear of claim 5 wherein the eyewear is a pair of sunglasses.

8. The eyewear of claim 6 wherein the pair of transparent lenses are formed from a single unitary piece of tinted polymeric material.

9. The eyewear of claim 8 wherein the nosepiece is formed from the polymeric material such that the lenses and the nosepiece are formed from the same unitary piece of polymeric material.

10. The eyewear of claim 1 wherein the nosepiece is conformable.

11. The eyewear of claim 1 wherein the deflectors will not extend over the auditory meatus of a wearer's ears when worn.

12. The eyewear of claim 5 wherein the bows and deflectors form right-side and left-side pairs, and each pair is hinged to a side of the frame so as to be effective for lateral rotation relative to the frame.

13. The eyewear of claim 5 wherein the deflectors are releasably hinged to the frame, whereby the deflectors can be attached, detached and reattached to the frame as desired.

14. The eyewear of claim 12 wherein the deflectors are releasably hinged to the frame, whereby the deflectors can be attached, detached and reattached to the frame as desired.

15. The eyewear of claim 14 wherein each deflector is releasably engaged to the paired bow, whereby the deflectors can be attached, detached and reattached to the paired bow as desired.

16. The sunglasses of claim 7 wherein the bows and deflectors form right side and left side pairs, and each pair is hinged to a side of the frame so as to be effective for lateral rotation relative to the frame.

17. The sunglasses of claim 7 wherein the deflectors are releasably hinged to the frame, whereby the deflectors can be attached, detached and reattached to the frame as desired.

18. The sunglasses of claim 16 wherein the deflectors are releasably hinged to the frame, whereby the deflectors can be attached, detached and reattached to the frame as desired.

19. The sunglasses of claim 18 wherein each deflector is releasably engaged to the paired bow, whereby the deflectors can be attached, detached and reattached to the paired bow as desired.

20. The sunglasses of claim 8 wherein the bows and deflectors form right-side and left-side pairs, and each pair is hinged to a side of the lenses so as to be effective for lateral rotation relative to the lenses.

21. The sunglasses of claim 8 wherein the deflectors are releasably hinged to the lenses, whereby the deflectors can be attached, detached and reattached to the lenses as desired.

22. The sunglasses of claim 20 wherein the deflectors are releasably hinged to the lenses, whereby the deflectors can be attached, detached and reattached to the lenses as desired.

23. The sunglasses of claim 22 wherein each deflector is releasably engaged to the paired bow, whereby the deflectors can be attached, detached and reattached to the paired bow as desired.

24. Wind-deflective eyewear, comprising:
   (a) a pair of transparent lenses formed from a unitary, polymeric material;
   (b) a nosepiece;
   (c) a rearwardly extending bow hingedly attached to each of the lenses so as to form a pair of conventional eyewear; and
   (d) a wind-deflecting deflector releasably hinged to each of the lenses and continuously extending rearward from each lense in substantially parallel relationship to the corresponding bow, wherein the deflectors are configured and arranged to guide rearwardly-directed air flow away from the auditory meatus of a wearer without covering the auditory meatus.

* * * * *